US009327973B1

(12) United States Patent
Tsai et al.

(10) Patent No.: US 9,327,973 B1
(45) Date of Patent: May 3, 2016

(54) METHODS AND APPARATUSES FOR REFORMING OF HYDROCARBONS INCLUDING RECOVERY OF PRODUCTS USING A RECOVERY ZONE, AN ABSORPTION ZONE AND A PRESSURE SWING ADSORPTION ZONE

(71) Applicant: UOP LLC, Des Plaines, IL (US)

(72) Inventors: Robert Edison Tsai, Arlington Heights, IL (US); Xin X. Zhu, Long Grove, IL (US); Tokhanh Ngo, Glendale Heights, IL (US); William Yanez, Crystal Lake, IL (US); Bryan K. Glover, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 75 days.

(21) Appl. No.: 14/524,291

(22) Filed: Oct. 27, 2014

(51) Int. Cl.
    *B01D 53/047*     (2006.01)
    *C01B 3/56*     (2006.01)
    *C07C 7/12*     (2006.01)
    (Continued)

(52) U.S. Cl.
CPC ............. *C01B 3/56* (2013.01); *B01D 53/047* (2013.01); *B01D 53/1437* (2013.01); *B01D 53/1487* (2013.01); *B01D 53/1493* (2013.01); *C07C 7/12* (2013.01); *C10L 3/12* (2013.01); *B01D 2256/16* (2013.01); *B01D 2257/108* (2013.01); *B01D 2257/702* (2013.01); *C01B 2203/042* (2013.01); *C01B 2203/048* (2013.01); *C10L 2290/542* (2013.01)

(58) Field of Classification Search
CPC ............ C01B 3/56; C01B 2203/042; C01B 2203/048; C01B 2290/542; B01D 53/047; B01D 53/1437; B01D 53/1487; B01D 53/1493; B01D 2256/16; B01D 2257/108; B01D 2257/702; C07C 7/12; C10L 3/12
USPC ............... 95/92, 96, 143, 237; 96/121, 243; 585/800, 820, 833; 208/99–101, 103, 208/341–343
See application file for complete search history.

(56) References Cited

U.S. PATENT DOCUMENTS 4,364,820 A     12/1982     DeGraff et al.
4,673,488 A     6/1987     Turner et al.
(Continued)

OTHER PUBLICATIONS

Mivechian et al., Performance Comparison of Different Separation Systems for H2 Recovery from Catalytic Reforming Unit Off-Gas Streams, Chemical Engineering and Technology, v 36, n 3, p. 519-527, Mar. 2013; ISSN: 09307516, E-ISSN: 15214125; DOI: 10.1002/ceat.201200558; Publisher: Wiley-VCH Verlag.

(Continued)

*Primary Examiner* — Frank Lawrence

(57) ABSTRACT

Embodiments of apparatuses and methods for reforming of hydrocarbons including recovery of products are provided. In one example, a method comprises separating a reforming-zone effluent into a net gas phase stream and a liquid phase hydrocarbon stream. The net gas phase stream is separated for forming an $H_2$-rich stream and a first intermediate liquid phase hydrocarbon stream. The $H_2$-rich stream is contacted with an adsorbent to form an $H_2$-ultra rich stream and a PSA tail gas stream. The PSA tail gas stream and at least a portion of the liquid phase hydrocarbon stream are cooled and contacted with each other to form a $H_2$, $C_2^-$ hydrocarbons-containing gas stream and a cooled second intermediate liquid phase hydrocarbon stream.

20 Claims, 3 Drawing Sheets

(51) Int. Cl.
*C10L 3/12* (2006.01)
*B01D 53/14* (2006.01)

(56) References Cited

U.S. PATENT DOCUMENTS

| | | |
|---|---|---|
| 5,332,492 A | 7/1994 | Maurer et al. |
| 5,411,721 A | 5/1995 | Doshi et al. |
| 6,171,472 B1 | 1/2001 | Lokhandwala et al. |
| 6,190,536 B1 | 2/2001 | Lokhandwala et al. |
| 6,350,371 B1 | 2/2002 | Lokhandwala et al. |
| 6,592,650 B2 | 7/2003 | Pinnau et al. |
| 7,452,458 B2 | 11/2008 | Sanchez et al. |
| 8,394,171 B2 | 3/2013 | Elseviers et al. |
| 8,455,555 B2 | 6/2013 | Chippenham et al. |
| 2014/0353215 A1* | 12/2014 | Glover ............... C10L 3/12 208/344 |
| 2015/0375160 A1* | 12/2015 | Tsai ............... B01D 53/047 95/96 |

OTHER PUBLICATIONS

Allen, Managing Hydrogen Recovery, International Journal of Hydrocarbon Engineering (ISSN 1364-3177) V4 N.4 71-75 (Apr. 1999), v 4, n 4, p. 71-75, Apr. 1999; ISSN: 13643177; Publisher: Palladian Publications.

* cited by examiner

METHODS AND APPARATUSES FOR REFORMING OF HYDROCARBONS INCLUDING RECOVERY OF PRODUCTS USING A RECOVERY ZONE, AN ABSORPTION ZONE AND A PRESSURE SWING ADSORPTION ZONE

TECHNICAL FIELD

The technical field relates generally to reforming of hydrocarbons, and more particularly relates to apparatuses and methods for reforming of hydrocarbons with improved recovery of products from a reforming-zone effluent.

BACKGROUND

High octane gasoline is needed for modern gasoline engines. Previously, octane numbers were often improved by incorporating various lead-containing additives into the gasoline. As lead-containing additives have been phased out of gasoline for environmental reasons, it has become increasingly necessary to rearrange the structure of the hydrocarbons used in gasoline blending to achieve higher octane ratings. Catalytic reforming of hydrocarbons is a process widely used by refiners for upgrading the octane ratings of gasoline as well as for other useful hydrocarbon conversion applications.

In catalytic reforming, a hydrocarbon feedstock of, for example, $C_5$ hydrocarbons to about $C_{11}$ hydrocarbons, is contacted with a reforming catalyst to convert at least a portion of the heavier hydrocarbons to aromatic hydrocarbons, for example, to increase the octane content of gasoline. The catalytic reforming of the heavier hydrocarbons to produce a reformate that includes aromatic hydrocarbons also produces significant quantities of valuable hydrogen and lighter hydrocarbons, such as liquefied petroleum gas (LPG) containing primarily $C_3$ and $C_4$ hydrocarbons. Refiners are looking for ways to maximize the recovery of reforming products, such as reformate, hydrogen and LPG, from the reforming reactor effluent.

Accordingly, it is desirable to provide apparatuses and methods for reforming of hydrocarbons with improved recovery of products from a reforming reactor effluent. Furthermore, other desirable features and characteristics will become apparent from the subsequent detailed description and the appended claims, taken in conjunction with the accompanying drawings and this background.

BRIEF SUMMARY

Apparatuses and methods for reforming of hydrocarbons including recovery of products are provided herein. In accordance with an exemplary embodiment, an apparatus for reforming of hydrocarbons including recovery of products comprises a separation zone. The separation zone is configured to receive and separate a reforming-zone effluent that comprises $H_2$, $C_4^-$ hydrocarbons, and $C_5^+$ hydrocarbons including aromatics to form a net gas phase stream that comprises $H_2$ and $C_6^-$ hydrocarbons and a liquid phase hydrocarbon stream that comprises $C_5^+$ hydrocarbons. A recovery zone is configured to receive and separate the net gas phase stream for forming an $H_2$-rich stream and a first intermediate liquid phase hydrocarbon stream. The first intermediate liquid phase hydrocarbon stream is enriched with $C_3/C_4$ hydrocarbons and further comprises $C_5^+$ hydrocarbons. A pressure swing adsorption (PSA) zone contains an adsorbent for selectively separating $H_2$ from hydrocarbons. The PSA zone is configured for receiving the $H_2$-rich stream and for contacting the $H_2$-rich stream with the adsorbent to form an $H_2$-ultra rich stream and a PSA tail gas stream that comprises $H_2$, $C_2^-$ hydrocarbons, and some $C_3^+$ hydrocarbons. An absorption zone is configured to receive and cool the PSA tail gas stream and at least a portion of the liquid phase hydrocarbon stream to form a cooled PSA tail gas stream and a cooled liquid phase hydrocarbon stream, respectively. The absorption zone comprises an absorber that is configured for contacting the cooled PSA tail gas stream with the cooled liquid phase hydrocarbon stream to extract $C_3/C_4$ hydrocarbons from the cooled PSA tail gas stream to the cooled liquid phase hydrocarbon stream to form a $H_2$, $C_2^-$ hydrocarbons-containing gas stream and a cooled second intermediate liquid phase hydrocarbon stream. The cooled second intermediate liquid phase hydrocarbon stream is enriched with $C_3/C_4$ hydrocarbons.

In accordance with another exemplary embodiment, a method for reforming of hydrocarbons including recovery of products is provided. The method comprises the steps of separating a reforming-zone effluent that comprises $H_2$, $C_4^-$ hydrocarbons, and $C_5^+$ hydrocarbons including aromatics to form a net gas phase stream that comprises $H_2$ and $C_6^-$ hydrocarbons and a liquid phase hydrocarbon stream that comprises $C_5^+$ hydrocarbons. The net gas phase stream is separated for forming an $H_2$-rich stream and a first intermediate liquid phase hydrocarbon stream. The first intermediate liquid phase hydrocarbon stream is enriched with $C_3/C_4$ hydrocarbons and further comprises $C_5^+$ hydrocarbons. The $H_2$-rich stream is contacted with an adsorbent that selectively separates $H_2$ from hydrocarbons to form an $H_2$-ultra rich stream and a pressure swing adsorption (PSA) tail gas stream that comprises $H_2$, $C_2^-$ hydrocarbons, and some $C_3^+$ hydrocarbons. The PSA tail gas stream is cooled to form a cooled PSA tail gas stream. At least a portion of the liquid phase hydrocarbon stream is cooled to form a cooled liquid phase hydrocarbon stream. The cooled PSA tail gas stream is contacted with the cooled liquid phase hydrocarbon stream to extract $C_3/C_4$ hydrocarbons from the cooled PSA tail gas stream to the cooled liquid phase hydrocarbon stream and to form a $H_2$, $C_2^-$ hydrocarbons-containing gas stream and a cooled second intermediate liquid phase hydrocarbon stream. The cooled second intermediate liquid phase hydrocarbon stream is enriched with $C_3/C_4$ hydrocarbons.

In accordance with another exemplary embodiment, a method for reforming of hydrocarbons including recovery of products is provided. The method comprises the steps of combining a gas phase stream that comprises $H_2$ and $C_6$ hydrocarbons with a first portion of a liquid phase hydrocarbon stream that comprises $C_5^+$ hydrocarbons including aromatics to extract $C_3/C_4$ hydrocarbons from the gas phase stream to the first portion of the liquid phase hydrocarbon stream for forming an $H_2$-rich stream and an intermediate liquid phase hydrocarbon stream. The $H_2$-rich stream comprises primarily $H_2$ and the intermediate liquid phase hydrocarbon stream is enriched with $C_3/C_4$ hydrocarbons and further comprises $C_5^+$ hydrocarbons. The $H_2$-rich stream is contacted with an adsorbent that selectively separates $H_2$ from hydrocarbons and that is contained in a pressure swing adsorption (PSA) zone to form an $H_2$-ultra rich stream and a PSA tail gas stream that comprises $H_2$, $C_2^-$ hydrocarbons, and some $C_3^+$ hydrocarbons. The PSA tail gas stream is cooled to form a cooled PSA tail gas stream. A second portion of the liquid phase hydrocarbon stream is cooled to form a cooled liquid phase hydrocarbon stream. The cooled PSA tail gas stream is contacted with the cooled liquid phase hydrocarbon stream in an absorber to extract $C_3/C_4$ hydrocarbons from the cooled PSA tail gas stream to the cooled liquid phase hydrocarbon stream and to form a $H_2$, $C_2^-$ hydrocarbons-containing gas stream and a cooled second intermediate liquid phase hydrocarbon stream that is enriched with $C_3/C_4$ hydrocarbons.

BRIEF DESCRIPTION OF THE DRAWINGS

The various embodiments will hereinafter be described in conjunction with the following drawing figures, wherein like numerals denote like elements, and wherein.

DETAILED DESCRIPTION

Figure 1:
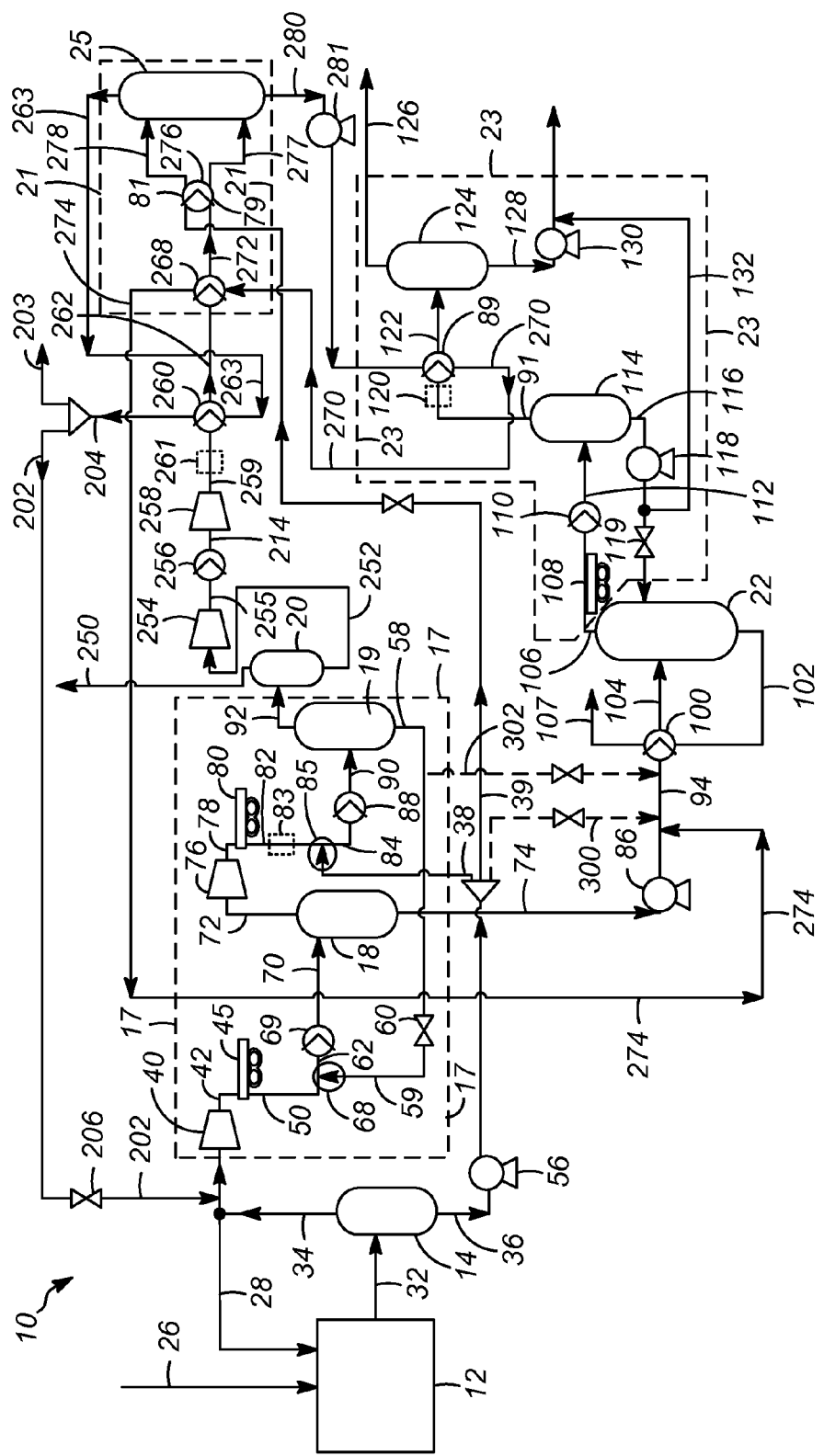
FIG. 1 schematically illustrates an apparatus and a method for reforming of hydrocarbons including recovery of products in accordance with an exemplary embodiment.

The following Detailed Description is merely exemplary in nature and is not intended to limit the various embodiments or the application and uses thereof.

Furthermore, there is no intention to be bound by any theory presented in the preceding background or the following detailed description.

Various embodiments contemplated herein relate to apparatuses and methods for reforming of hydrocarbons with improved recovery of products from a reforming-zone effluent. The exemplary embodiments taught herein provide a separation zone in fluid communication with a reforming zone to receive a reforming-zone effluent. As used herein, the term "zone" refers to an area including one or more equipment items and/or one or more sub-zones. Equipment items can include one or more reactors or reactor vessels, scrubbers, strippers, fractionators or distillation columns, absorbers or absorber vessels, regenerators, heaters, exchangers, coolers/chillers, pipes, pumps, compressors, controllers, and the like. Additionally, an equipment item can further include one or more zones or sub-zones. The reforming-zone effluent comprises hydrogen ($H_2$), $C_4$ hydrocarbons, and $C_5^+$ hydrocarbons including aromatics. As used herein, $C_x$ means hydrocarbon molecules that have "X" number of carbon atoms, $C_x^+$ means hydrocarbon molecules that have "X" and/or more than "X" number of carbon atoms, and $C_x^-$ means hydrocarbon molecules that have "X" and/or less than "X" number of carbon atoms.

The separation zone separates the reforming-zone effluent to form a net gas phase stream and a liquid phase hydrocarbon stream. The net gas phase stream comprises $H_2$ and $C_6$ hydrocarbons and the liquid phase hydrocarbon stream comprises $C_5^+$ hydrocarbons.

In a recovery zone, the net gas phase stream is separated to form an $H_2$-rich stream and a first intermediate liquid phase hydrocarbon stream. In one example, in the recovery zone, the net gas phase stream and a first portion of the liquid phase hydrocarbon stream are combined to extract $C_3/C_4$ hydrocarbons from the net gas phase stream to the first portion of the liquid phase hydrocarbon stream and to form a first two-phase combined stream. In an exemplary embodiment, the first two-phase combined stream is partially cooled and separated into the $H_2$-rich stream and the first intermediate liquid phase hydrocarbon stream. The first intermediate liquid phase hydrocarbon stream is enriched with $C_3/C_4$ hydrocarbons and further comprises $C_5^+$ hydrocarbons including aromatics. As used herein, the term "rich" means the corresponding component(s) is present in an amount of about 70 mole percent (mole %) or greater, such as about 80 mole % or greater. As used herein, the term "enriched" means that the concentration of the corresponding component(s) has increased relative to its original or previous concentration.

In an exemplary embodiment, the $H_2$-rich stream is passed along to a pressure swing adsorption (PSA) zone that contains an adsorbent for selectively separating $H_2$ from hydrocarbons. In the PSA zone, the $H_2$-rich stream is contacted with the adsorbent to form an $H_2$-ultra rich stream and a PSA tail gas stream that comprises $H_2$, $C_2^-$ hydrocarbons, and some $C_3^+$ hydrocarbons. As used herein, the term "ultra rich" means about 90 mole % or greater. As used herein, the term "some" means less than about 50 mole %, such as 40 mole % or less, such as 30 mole % or less, such as 20 mole % or less, such as 10 mole % or less, for example from about 10 to about 0.01 mole %.

In an absorption zone, the PSA tail gas stream and at least a portion of the liquid phase hydrocarbon stream are cooled to form a cooled PSA tail gas stream and a cooled liquid phase hydrocarbon stream, respectively. In one example, the PSA tail gas stream and a second portion of the liquid phase hydrocarbon stream are cooled to form the cooled PSA tail gas stream and the cooled liquid phase hydrocarbon stream, respectively. In an exemplary embodiment, the absorption zone includes an absorber in which the cooled PSA tail gas stream is contacted with the cooled liquid phase hydrocarbon stream, for example, in countercurrent contacting flow, to extract $C_3/C_4$ hydrocarbons from the cooled PSA tail gas stream to the cooled liquid phase hydrocarbon stream to form a $H_2$, $C_2^-$ hydrocarbons-containing gas stream and a cooled second intermediate liquid phase hydrocarbon stream. The cooled second intermediate liquid phase hydrocarbon stream is enriched with $C_3/C_4$ hydrocarbons and further comprises $C_5^+$ hydrocarbons including aromatics.

In an exemplary embodiment, the cooled second intermediate liquid phase hydrocarbon stream is passed through at least one heater and/or heat exchanger(s) to form a heated second intermediate liquid phase hydrocarbon stream. The heated second intermediate liquid phase hydrocarbon stream is separated in a stabilizer to form a $C_5^+$ hydrocarbon-rich reformate stream that comprises primarily $C_5^+$ hydrocarbons including aromatics and a stabilizer gas stream that comprises $H_2$ and $C_4$ hydrocarbons. As used herein, the term "primarily" means about 50 mole % or greater. A stabilizer gas separation zone partially condenses, cools and further separates at least a portion of the stabilizer gas stream to form a $C_3/C_4$ hydrocarbon-rich LPG stream that comprises primarily $C_3/C_4$ hydrocarbons and a light ends gas stream that comprises $H_2$ and $C_2^-$ hydrocarbons.

Referring to FIG. 1, an apparatus 10 for reforming of hydrocarbons in accordance with an exemplary embodiment is provided. The apparatus 10 comprises a reforming zone 12, a separation zone 14, a recovery zone 17 including recontact drums 18 and 19, a pressure swing adsorption (PSA) zone 20, an absorption zone 21 including an absorber 25 (e.g., multistage vessel or separation vessel that contains trays or packing), a stabilizer 22, and a stabilizer gas separation zone 23 that are in fluid communication.

In an exemplary embodiment, a reforming-zone feedstock 26 containing naphtha fraction hydrocarbons, such as from $C_5$ to about $C_{11}$ hydrocarbons with a boiling point range of, for example, from about 70 to about 205° C., is introduced to the apparatus 10. The reforming-zone feedstock 26 and a recycle net gas phase stream 28 (discussed in further detail below) are passed along to the reforming zone 12 that contains a reforming catalyst as is well-known in the art. The reforming zone 12 will typically comprise a plurality of stacked or side-by-side reactors with provisions for intermediate heating of the intermediate reactant stream (e.g., the reforming-zone feedstock 26 and the recycle net gas phase stream 28 including any conversion products formed therefrom) and one or more heat exchangers. In an exemplary embodiment, in the reforming zone 12, the recycle net gas phase stream 28 is combined with the reforming-zone feedstock 26 for contact with the reforming catalyst.

A reforming-zone effluent 32 is formed in the reforming zone 12 and contains $H_2$, $C_5^+$ hydrocarbons including aromatics, and lighter hydrocarbons such as $C_4^-$ hydrocarbons including $C_3$ and $C_4$ hydrocarbons. In an exemplary embodiment, the reforming-zone effluent 32 is a two-phase liquid-gas stream in which $H_2$ and the lighter hydrocarbons (e.g., $C_4^-$ hydrocarbons) are predominately in the gas phase and the heavier hydrocarbons (e.g., $C_5^+$ hydrocarbons including aromatics) are predominately in the liquid phase. In one embodiment, the reforming-zone effluent 32 has a temperature of from about 35 to about 50° C. and, independently, a pressure of from about 240 to about 830 kPa gauge.

The reforming-zone effluent 32 is introduced to the separation zone 14. The separation zone 14 separates the reforming-zone effluent 32 into net gas phase stream 34 and a liquid phase hydrocarbon stream 36. In an exemplary embodiment, the net gas phase stream 34 comprises $H_2$ and $C_6$ hydrocarbons and the liquid phase hydrocarbon stream 36 comprises $C_5^+$ hydrocarbons including aromatics. In one example, the net gas phase stream 34 comprises $H_2$ present in an amount of from about 80 to about 90 mole %, $C_1$ hydrocarbons present in an amount of about 2 to about 5 mole %, $C_2$ hydrocarbons present in an amount of from about 2 to about 5 mole %, $C_3$ hydrocarbons present in an amount of from about 2 to about 4 mole %, $C_4$ hydrocarbons present in an amount of from about 1.5 to about 2.5 mole %, and possibly some $C_5^+$ hydrocarbons. In another example, the liquid phase hydrocarbon stream 36 comprises $C_5^+$ hydrocarbons present in an amount of from about 90 to about 99.9 mole % and some $C_4$ hydrocarbons and $H_2$. In an exemplary embodiment, the separation zone 14 is operated at a temperature of from about 35 to about 50° C. and, independently, a pressure of from about 240 to about 830 kPa gauge.

A portion of the net gas phase stream 34 is passed back to the reforming zone 12 as the recycle net gas phase stream 28 (as discussed above) and a remaining portion of the net gas phase stream 34 is passed along to the recovery zone 17 and introduced to a compressor 40. As illustrated and will be discussed in further detail below, in an exemplary embodiment, a recycle portion 202 of a $H_2$, $C_2^-$ hydrocarbons-containing gas stream 204 is passed through a valve 206 and is introduced to the net gas phase stream 34 upstream from the compressor 40. Although not illustrated, alternatively the recycle portion 202 may be passed along to other locations in the recovery zone 17, such as, for example, stream 72, which is discussed in further detail below. The compressor 40 compresses the net gas phase stream 34 including the recycle portion 202 to form a compressed net gas phase stream 42. In an exemplary embodiment, the compressed net gas phase stream 42 has a temperature of from about 120 to about 150° C. and, independently, a pressure of from about 720 to about 2,490 kPa gauge.

The compressed net gas phase stream 42 is passed along to a cooler 45. In the cooler 45, the compressed net gas phase stream 42 is partially cooled to form a partially cooled, compressed net gas phase stream 50. In an exemplary embodiment, the partially cooled, compressed net gas phase stream 50 has a temperature of from about 30 to about 65° C. and, independently, a pressure of from about 690 to about 2,460 kPa gauge.

In an exemplary embodiment, the liquid phase hydrocarbon stream 36 exits the separation zone 14 and is passed through a pump 56 and divided into portions 38 and 39, and optionally portion 300 discussed in further detail below. The portion 38 of the liquid phase hydrocarbon stream 36 is introduced to the recovery zone 17. The recovery zone 17 may be configured as a countercurrent gas and liquid phase recovery zone for further separating $H_2$, $C_3/C_4$ hydrocarbons, and/or $C_5^+$ hydrocarbons via extraction and/or absorption by contacting the liquid and gas phase fractions of the net gas phase stream 34 and the liquid phase hydrocarbon stream 36. Alternatively, the recovery zone 17 is not limited to countercurrent flow and that other modes, such as co-current modes as are known in the art, may be used for the recovery zone 17.

In an exemplary embodiment, in the recovery zone 17, the portion 38 of the liquid phase hydrocarbon stream 36 is enriched with $C_3/C_4$ hydrocarbons from the partially cooled, compressed net gas phase stream 50 and is cooled, which is discussed in further detail below, to form an intermediate liquid phase hydrocarbon stream 58. In an exemplary embodiment, the intermediate liquid phase hydrocarbon stream 58 comprises $C_3/C_4$ hydrocarbons and is rich in $C_5^+$ hydrocarbons. In an exemplary embodiment, the intermediate liquid phase hydrocarbon stream 58 is passed through a valve 60 to reduce pressure and form an intermediate liquid phase hydrocarbon stream 59. In an exemplary embodiment, the intermediate liquid phase hydrocarbon stream 59 has a temperature of from about 4 to about 50° C. and, independently, a pressure of from about 690 to about 2,460 kPa gauge.

The intermediate liquid phase hydrocarbon stream 59 is introduced to the partially cooled, compressed net gas phase stream 50 to form a two-phase combined stream 62. Optionally, the recovery zone 17 includes a mixing device 68 that mixes the intermediate liquid phase hydrocarbon stream 59 with the partially cooled, compressed net gas phase stream 50 to form the two-phase combined stream 62. In an exemplary embodiment, the mixing device 68 aggressively mixes or homogenizes the partially cooled, compressed net gas phase stream 50 into the intermediate liquid phase hydrocarbon stream 59 such that the gas phase is broken up into a plurality of small bubbles that are well dispersed in turbulent flow with a $C_5^+$ hydrocarbon-rich liquid phase so that $C_3/C_4$ hydrocarbons are readily extracted from the gas phase to the $C_5^+$ hydrocarbon-rich liquid phase. As such, the two-phase combined stream 62 has a gas phase that is rich in $H_2$ and substantially depleted of $C_3^+$ hydrocarbons and a liquid phase that is rich in $C_3^+$ hydrocarbons.

The mixing device 68 may be a static mixer, a jet mixer, or the like. In an exemplary embodiment, the mixing device 68 is a jet mixer and the intermediate liquid phase hydrocarbon stream 59 is a motive liquid at a higher pressure than the partially cooled, compressed net gas phase stream 50 such that the motive liquid moves rapidly through the jet mixer causing the partially cooled, compressed net gas phase stream 50 to be sucked into the jet mixer by a "Venturi effect," such as occurs in an eductor or ejector, as a suction fluid to homogenize the partially cooled, compressed net gas phase stream 50 in the intermediate liquid phase hydrocarbon stream 59.

As illustrated, the two-phase combined stream 62 is passed through a cooler 69 to form a partially cooled two-phase combined stream 70. In an exemplary embodiment, the partially cooled two-phase combined stream 70 has a temperature of from about 20 to about 50° C. and, independently, a pressure of from about 660 to about 2,430 kPa gauge.

The partially cooled two-phase combined stream 70 is introduced to the recontact drum 18. While the recovery zone 17 is illustrated as only having 2 recontact drums 18 and 19, it is to be understood that the recovery zone 17 can have more than 2 recontact drums or only a single recontact drum. The partially cooled two-phase combined stream 70 is separated in the recontact drum 18 into its corresponding gas and liquid phases to form an intermediate gas phase stream 72 that comprises $H_2$ and $C_6$ hydrocarbons and an intermediate liquid phase hydrocarbon stream 74 that comprises $C_3^+$ hydrocarbons. In an exemplary embodiment, the intermediate gas phase stream 72 and, independently, the intermediate liquid phase hydrocarbon stream 74 each have a temperature of from about 20 to about 50° C. and, independently, a pressure of from about 660 to about 2,430 kPa gauge.

The intermediate gas phase stream 72 exits the recontact drum 18 and is passed along to a compressor 76. The compressor 76 compresses the intermediate gas phase stream 72 to form a compressed intermediate gas phase stream 78. In an exemplary embodiment, the compressed intermediate gas phase stream 78 has a temperature of from about 120 to about 160° C. and, independently, a pressure of from about 1,980 to about 5,580 kPa gauge.

The compressed intermediate gas phase stream 78 is introduced to a cooler 80 to form a partially cooled, compressed intermediate gas phase stream 82. In an exemplary embodiment, the partially cooled, compressed intermediate gas phase stream 82 has a temperature of from about 30 to about 65° C. and, independently, a pressure of from about 1,950 to about 5,550 kPa gauge.

The partially cooled, compressed intermediate gas phase stream 82 exits the cooler 80 and optionally, is passed through a dryer 83 (e.g., vessel with adsorbent material or the like adsorbing water or otherwise removing water) for removing water from the partially cooled, compressed intermediate gas phase stream 82 to help avoid the formation of hydrates. In an exemplary embodiment, upstream from the dryer 83, the partially cooled, compressed intermediate gas phase stream 82 includes water present in an amount of about 15 ppm by weight or greater, and after being passed through the dryer 83, the partially cooled, compressed intermediate gas phase stream 82 includes water present in an amount of less than about 15 ppm by weight.

Next, the partially cooled, compressed intermediate gas phase stream 82 is combined with the portion 38 of the liquid phase hydrocarbon stream 36 to form an intermediate two-phase combined stream 84. Optionally, in an exemplary embodiment, the apparatus 10 comprises a mixing device 85 (e.g., similarly configured to the mixing device 68 as discussed above) for aggressively mixing or homogenizing the partially cooled, compressed intermediate gas phase stream 82 into the portion 38 of the liquid phase hydrocarbon stream 36. As such, the partially cooled, compressed intermediate gas phase stream 82 is broken up into a plurality of small bubbles that are well dispersed in turbulent flow with a $C_5^+$ hydrocarbon-rich liquid phase of the portion 38 of the liquid phase hydrocarbon stream 36 so that $C_3/C_4$ hydrocarbons are readily extracted from the gas phase to the $C_5^+$ hydrocarbon-rich liquid phase. In an exemplary embodiment, the intermediate two-phase combined stream 84 has a gas phase that is rich in $H_2$ and substantially depleted of $C_3^+$ hydrocarbons and a liquid phase that is rich in $C_3^+$ hydrocarbons.

The intermediate two-phase combined stream 84 is passed along and introduced to a cooler 88. The cooler 88 partially cools the intermediate two-phase combined stream 84 to form a partially cooled intermediate two-phase combined stream 90. In an exemplary embodiment, the partially cooled intermediate two-phase combined stream 90 has a temperature of from about 4 to about 50° C. and, independently, a pressure of from about 1,920 to about 5,520 kPa gauge.

The partially cooled intermediate two-phase combined stream 90 is introduced to the recontact drum 19. The partially cooled intermediate two-phase combined stream 90 is separated in the recontact drum 19 into its corresponding gas and liquid phases to form an $H_2$-rich stream 92 that comprises primarily $H_2$ and the intermediate liquid phase hydrocarbon stream 58 as discussed above. In an exemplary embodiment, the $H_2$-rich stream 92 and, independently, the intermediate liquid phase hydrocarbon stream 58 each have a temperature of from about 4 to about 50° C. and, independently, a pressure of from about 1,920 to about 5,520 kPa gauge. In an exemplary embodiment, the $H_2$-rich stream 92 comprises $H_2$ present in an amount of from about 80 to about 95 mole % with possibly some $C_4$ hydrocarbons.

The $H_2$-rich stream 92 is introduced to the PSA zone 20 for further purifying the stream 92 by removing hydrocarbons to form an $H_2$-ultra rich stream 250. In an exemplary embodiment, the PSA zone 20 contains an adsorbent (e.g., adsorbent material(s)) and is configured for contacting the $H_2$-rich stream 92 with the adsorbent for selectively separating $H_2$ from hydrocarbons (e.g., $C_4$ hydrocarbons) to form the $H_2$-ultra rich stream 250. The exemplary PSA zone 20 operates on the principle of selectively adsorbing hydrocarbons and/or other impurities onto the adsorbent at a relatively high pressure (e.g., about 1,920 to about 5,520 kPa gauge) to form the $H_2$-ultra rich stream 250, and desorbing the hydrocarbons from the adsorbent at relatively low pressure (e.g., about 10 to about 500 kPa gauge) to regenerate the adsorbent and to form a PSA tail gas stream 252 that contains the hydrocarbons and/or other impurities.

In an exemplary embodiment, the PSA zone 20 includes a plurality of fixed-bed adsorption units each containing layers of different adsorbent materials where the lower layer or layers are filled with weaker adsorbent materials, e.g., relatively low affinity for adsorbing gaseous hydrocarbons, and the upper layer or layers are filled with stronger adsorbent materials, e.g., relatively high affinity for adsorbing gaseous hydrocarbons. For example, the lower layer(s) can contain weakly adsorbent materials, such as activated alumina and/or silica gel, while the intermediate layer(s) can contain intermediate strength adsorbent materials, such as activated carbon, and the upper layer(s) can contain strong adsorbent materials, such as zeolite and/or molecular sieve materials. In an exemplary embodiment, the multiple fixed-bed adsorption units cooperatively operate in a staggered sequence to produce constant feed (e.g., the $H_2$-rich stream 92), product (e.g., the $H_2$-ultra rich stream 250), and tail gas (e.g., the PSA tail gas stream 252) flows. In an exemplary embodiment, the PSA zone 20 operates following a five-step pressure-swing cycle including an adsorption step, a co-current depressurization step, a counter-current depressurization step, a purge step, and a repressurization step. During the adsorption step, the $H_2$-rich stream 92 enters a lower portion of the fixed-bed adsorption unit at a relatively high pressure, and as the feed gas rises in the unit, the hydrocarbons are adsorbed in the various layers of the adsorbent materials depending upon their respective adsorption selectivity to form the $H_2$-ultra rich stream 250. The co-current depressurization, counter-current depressurization and purge steps decrease the pressure in the fixed-bed adsorption unit and purge the unit with high purity gas from the product (e.g., the $H_2$-ultra rich stream 250) or co-current depressurization steps, respectively, to remove the hydrocarbons and regenerate the adsorption materials. The repressurization step increases the pressure in the fixed-bed adsorption unit with either feed gas (e.g., the $H_2$-rich stream 92) or product gas (e.g., the $H_2$-ultra rich stream 250) in preparation for the next adsorption step. Other pressure swing adsorption configurations for forming an $H_2$-ultra rich stream known to those skilled in the art may also be used.

In an exemplary embodiment, the $H_2$-ultra rich stream 250 comprises $H_2$ present in an amount of from about 90 to less than 100 mole %, such as from about 90 to about 99.999 mole %, such as from about 95 to about 99.999 mole %, such as from about 98 to about 99.999 mole %, such as from about 99 to about 99.999 mole %, for example about 99.99 mole %, and possibly some $C_2^-$ hydrocarbons. In an exemplary embodiment, the $H_2$-rich stream 250 has a temperature of from about 30 to about 50° C. and, independently, a pressure of from about 1,880 to about 5,480 kPa gauge, for example about 2,070 to about 2,410 kPa gauge. In an exemplary embodiment, the PSA tail gas stream 252 comprises $C_2^-$ hydrocarbons present in an amount of from about 25 to about 80 mole %, $H_2$ present in an amount of from about 25 to about 75 mole %, and possibly some $C_3^+$ hydrocarbons. In an exemplary embodiment, the PSA tail gas stream 252 has a temperature of from about 30 to about 50° C. and, independently, a pressure of from about 10 to about 500 kPa gauge, for example about 20 to about 50 kPa gauge.

The $H_2$-ultra rich stream 250 is removed from the apparatus 10, for example, to be used as a hydrogen product stream. The PSA tail gas stream 252 is passed through a compressor 254 to form a compressed PSA tail gas stream 255 that is further advanced through a cooler 256 to partially cool the stream 255 and form a partially cooled, compressed PSA tail gas stream 214. In an exemplary embodiment, the partially cooled, compressed PSA tail gas stream 214 has a temperature of from about 30 to about 60° C. and, independently, a pressure of from about 690 to about 1,380 kPa gauge, for example of from about 690 to about 800 kPa gauge.

As illustrated, the partially cooled, compressed PSA tail gas stream 214 is passed through a compressor 258 to form a partially cooled, further compressed PSA tail gas stream 259. In an exemplary embodiment, optionally, the partially cooled, further compressed PSA tail gas stream 259 is passed through a dryer 261 for removing water from the partially cooled, further compressed PSA tail gas stream 259 to help avoid the formation of hydrates. In an exemplary embodiment, upstream from the dryer 261, the partially cooled, further compressed PSA tail gas stream 259 includes water present in an amount of about 15 ppm by weight or greater, and after being passed through the dryer 261, the partially cooled, further compressed PSA tail gas stream 259 includes water present in an amount of less than about 15 ppm by weight.

Next, the partially cooled, further compressed PSA tail gas stream 259 is passed through a PSA tail gas heat exchanger 260 for indirect heat exchange with an $H_2$, $C_2^-$ hydrocarbons-containing gas stream 263, which is discussed in further detail below, to form a further partially cooled, further compressed PSA tail gas stream 262 and the $H_2$, $C_2^-$ hydrocarbons-containing gas stream 204. In an exemplary embodiment, the further partially cooled, further compressed PSA tail gas stream 262 has a temperature of from about 30 to about 150° C. and, independently, a pressure of from about 690 to about 2,760 kPa gauge. In an exemplary embodiment, the $H_2$, $C_2^-$ hydrocarbons-containing gas stream 204 has a temperature of from about –12 to about 85° C. and, independently, a pressure of from about 600 to about 2,670 kPa gauge. As illustrated, the $H_2$, $C_2^-$ hydrocarbons-containing gas stream 204 is divided into the recycle portion 202 as discussed above and a portion 203 that may be removed from the apparatus 10, for example, to be used as fuel gas.

The further partially cooled, further compressed PSA tail gas stream 262 and the portion 39 of the liquid phase hydrocarbon stream 36 are introduced to the absorption zone 21. In an exemplary embodiment, the absorption zone 21 is configured as a countercurrent gas and liquid phase absorption zone for further separating $H_2$, $C_3/C_4$ hydrocarbons, and/or $C_5^+$ hydrocarbons via extraction and/or absorption by contacting the liquid and gas phase fractions of the further partially cooled, further compressed PSA tail gas stream 262 and the portion 39 of the liquid phase hydrocarbon stream 36. As illustrated, in an exemplary embodiment, the absorption zone 21 comprises a single absorber 25 as well as other types of equipment items as will be described in further detail below. Alternatively, the absorption zone 21 may have more than one absorber as well as other types of equipment items.

The further partially cooled, further compressed PSA tail gas stream 262 is passed along to an absorption zone heat exchanger 268 for indirect heat exchange with a partially heated, second intermediate liquid phase hydrocarbon stream 270 to form a further partially cooled, further compressed PSA tail gas stream 272 and a partially heated, second intermediate liquid phase hydrocarbon stream 274. In an exemplary embodiment, the further partially cooled, further compressed PSA tail gas stream 272 has a temperature of from about 20 to about 45° C. and, independently, a pressure of from about 660 to about 2,730 kPa gauge. In an exemplary embodiment, the partially heated, second intermediate liquid phase hydrocarbon stream 274 has a temperature of from about 30 to about 150° C. and, independently, a pressure of from about 1,000 to about 1,500 kPa gauge.

The further partially cooled, further compressed PSA tail gas stream 272 is passed along to a dual-bundle chiller 276 that has a chiller section 79 and a chiller section 81 each configured for cooling. Alternatively, chiller sections 79 and 81 may be corresponding chiller sections in separate chillers. The further partially cooled, further compressed PSA tail gas stream 272 is passed through the chiller section 79 to further cool the stream 272 and form a cooled PSA tail gas stream 277. In an exemplary embodiment, the cooled PSA tail gas stream 277 has a temperature of from about –28 to about 4° C., independently, a pressure of from about 630 to about 2,700 kPa gauge.

As illustrated, the portion 39 of the liquid phase hydrocarbon stream 36 is introduced to the dual-bundle chiller 276. The portion 39 of the liquid phase hydrocarbon stream 36 is passed through the chiller section 81 to cool the portion 39 and form a cooled liquid phase hydrocarbon stream 278. In an exemplary embodiment, the cooled liquid phase hydrocarbon stream 278 has a temperature of from about –28 to about 4° C., and independently, a pressure of from about 630 to about 2,700 kPa gauge.

The cooled PSA tail gas stream 277 and the cooled liquid phase hydrocarbon stream 278 are introduced to the absorber 25. As illustrated, in an exemplary embodiment, the cooled PSA tail gas stream 277 is introduced to a lower portion of the absorber 25 and rises upwardly while the cooled liquid phase hydrocarbon stream 278 is introduced to an upper portion of the absorber 25 and descends downwardly for countercurrent contact with the cooled PSA tail gas stream 277. During contact in the absorber 25, $C_3/C_4$ hydrocarbons from the cooled PSA tail gas stream 277 are extracted and/or absorbed to the cooled liquid phase hydrocarbon stream 278 to form a cooled second intermediate liquid phase hydrocarbon stream 280 that is enriched with $C_3/C_4$ hydrocarbons and further comprises $C_5^+$ hydrocarbons and the $H_2$, $C_2^-$ hydrocarbons-containing gas stream 263. In an exemplary embodiment, the cooled second intermediate liquid phase hydrocarbon stream 280 and, independently, the $H_2$, $C_2^-$ hydrocarbons-containing gas stream 263 each have a temperature of from about −28 to about 4° C. and, independently, a pressure of from about 630 to about 2,700 kPa gauge.

In an exemplary embodiment, the cooled second intermediate liquid phase hydrocarbon stream 280 is optionally passed through a pump 281 and is introduced to the stabilizer gas separation zone 23. The cooled second intermediate liquid phase hydrocarbon stream 280 is passed through a stabilizer gas separation zone heat exchanger 89 for indirect heat exchange with a stabilizer net gas stream 91, which is discussed in further detail below, to form the partially heated, second intermediate liquid phase hydrocarbon stream 270. In an exemplary embodiment, the partially heated, second intermediate liquid phase hydrocarbon stream 270 has a temperature of from about 15 to about 65° C. and, independently, a pressure of from about 1,100 to about 1,600 kPa gauge.

As discussed above, the partially heated, second intermediate liquid phase hydrocarbon stream 270 is passed through the absorption zone heat exchanger 268 to form the partially heated, second intermediate liquid phase hydrocarbon stream 274. The intermediate liquid phase hydrocarbon stream 74 exits the recontact drum 18, is optionally passed through a pump 86, and is combined with the partially heated, second intermediate liquid phase hydrocarbon stream 274 to form a combined liquid phase hydrocarbon stream 94. Optionally, the combined liquid phase hydrocarbon stream 94 may also include a corresponding portion(s) from the liquid phase hydrocarbon stream 36 and/or the intermediate liquid phase hydrocarbon stream 58 via line 300 and/or line 302, respectively. In an exemplary embodiment, the combined liquid phase hydrocarbon stream 94 has a temperature of from about 20 to about 150° C. and, independently, a pressure of from about 1,000 to about 1,500 kPa gauge.

The combined liquid phase hydrocarbon stream 94 is passed through a stabilizer heat exchanger 100 for indirect heat exchange with a $C_5^+$ hydrocarbon-rich reformate stream 102, which is discussed in further detail below, to form a heated intermediate liquid phase hydrocarbon stream 104. In an exemplary embodiment, the heated intermediate liquid phase hydrocarbon stream 104 has a temperature of from about 150 to about 200° C. and, independently, a pressure of from about 900 to about 1,400 kPa gauge.

The heated intermediate liquid phase hydrocarbon stream 104 is passed along to the stabilizer 22. The stabilizer 22 separates the heated intermediate liquid phase hydrocarbon stream 104 into a stabilizer gas stream 106 that comprises $H_2$ and $C_4$ hydrocarbons enriched with $C_3/C_4$ hydrocarbons and the $C_5^+$ hydrocarbon-rich reformate stream 102. In an exemplary embodiment, the $C_5^+$ hydrocarbon-rich reformate stream 102 comprises $C_5^+$ hydrocarbons including aromatics present in an amount of about 90 to about 99.9 mole %. As discussed above, the $C_5^+$ hydrocarbon-rich reformate stream 102 is passed through the stabilizer heat exchanger 100 and is removed from the apparatus 10 as a reformate product 107.

The stabilizer gas stream 106 is introduced to the stabilizer gas separation zone 23 and is passed through a first cooler 108 (e.g., an air cooler) and a second cooler 110 (e.g., a water cooler) to partially condense and cool the stream 106 and form a partially condensed stabilizer gas stream 112. In an exemplary embodiment, the partially condensed stabilizer gas stream 112 has a temperature of from about 30 to about 65° C. and, independently, a pressure of from about 800 to about 1,300 kPa gauge.

The partially condensed stabilizer gas stream 112 is passed along to a receiver 114 to remove condensed/liquid hydrocarbons from the stream 112 and to form the stabilizer net gas stream 91 as discussed above and a $C_3^+$ hydrocarbons-containing liquid phase stream 116. The $C_3^+$ hydrocarbons-containing liquid phase stream 116 exits the receiver 114 and is passed along through a pump 118 and a valve 119 back to the stabilizer 22 as a recycle stream.

The stabilizer net gas stream 91 is passed towards the stabilizer gas separation zone heat exchanger 89. Optionally, in an exemplary embodiment, the stabilizer gas separation zone 23 includes a dryer 120 upstream from the stabilizer gas separation zone heat exchanger 89 for removing water from the stabilizer net gas stream 91 to help avoid the formation of hydrates. In an exemplary embodiment, upstream from the dryer 120, the stabilizer net gas stream 91 includes water present in an amount of about 15 ppm by weight or greater, and after being passed through the dryer 120, the stabilizer net gas stream 91 includes water present in an amount of less than about 15 ppm by weight.

As discussed above, the stabilizer net gas stream 91 is passed through the stabilizer gas separation zone heat exchanger 89 for indirect heat exchange with the cooled second intermediate liquid phase hydrocarbon stream 280 to partially condense and cool the stream 91 and to form a partially condensed stabilizer net gas stream 122. Although the stabilizer net gas stream 91 is shown as being passed through only a single stabilizer gas separation zone heat exchanger 89, the stream 91 may be partially condensed and cooled by being advanced through one or more heat exchangers, chillers, coolers, or combination thereof. In an exemplary embodiment, the partially condensed stabilizer net gas stream 122 has a temperature of from about −28 to about 4° C., for example, from about −12 to about 0° C. and, independently, a pressure of from about 700 to about 1,200 kPa gauge.

The partially condensed stabilizer net gas stream 122 is introduced to a separator 124. The separator 124 may be configured as a flash drum, or alternatively, may be configured as a multi-stage fractionation tower. The separator 124 separates $C_3/C_4$ hydrocarbons and any remaining $H_2$ and $C_2^-$ hydrocarbons from the partially condensed stabilizer net gas stream 122 to form a light ends gas stream 126 and a $C_3/C_4$ hydrocarbon-rich LPG stream 128. In an exemplary embodiment, the $C_3/C_4$ hydrocarbon-rich LPG stream 128 comprises $C_3/C_4$ hydrocarbons present in an amount of about 70 to about 99.9 mole % and the light ends gas stream 126 comprises $H_2$ present in an amount of from about 1 to about 50 mole %, $C_2^-$ hydrocarbons present in an amount of from about 20 to about 60 mole %, and possibly some $C_3^+$ hydrocarbons. As illustrated, the $C_3/C_4$ hydrocarbon-rich LPG stream 128 is passed through a pump 130, is optionally combined with a side stream 132 of the $C_3^+$ hydrocarbons-containing liquid phase stream 116, and is removed from the apparatus 10 as an LPG product stream. The light ends gas stream 126 is removed from the apparatus 10 to be used, for example, as fuel gas.

Figure 2:
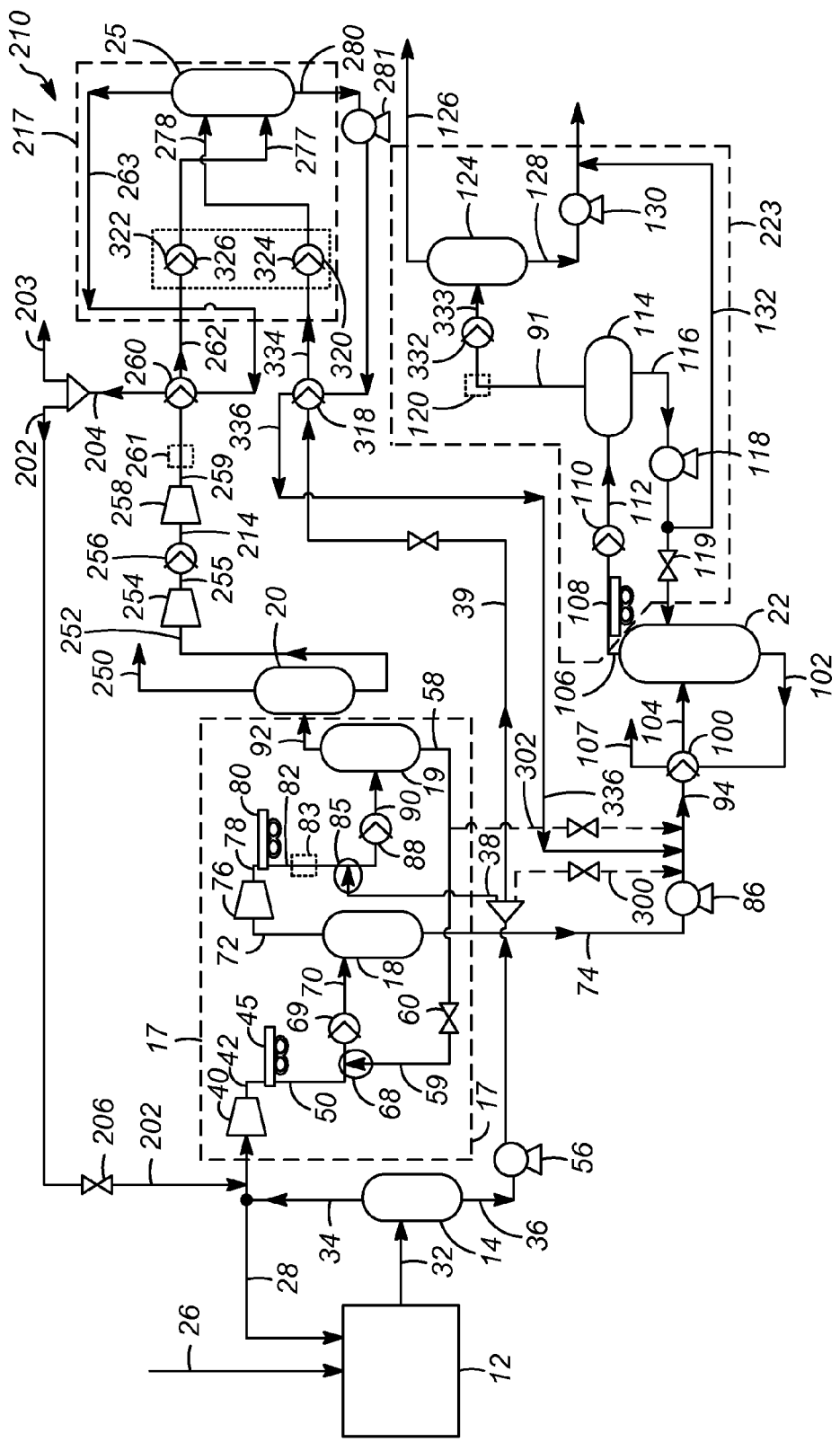
FIG. 2 schematically illustrates an apparatus and a method for reforming of hydrocarbons including recovery of products in accordance with another exemplary embodiment.

Referring to FIG. 2, an apparatus 210 for reforming of hydrocarbons in accordance with another exemplary embodiment is provided. The apparatus 210 is similarly configured to the apparatus 10 including the reforming zone 12, the separation zone 14, the recovery zone 17 including the recontact drums 18 and 19, the PSA zone 20, the absorption zone 217 including the absorber 25, the stabilizer 22, and the stabilizer gas separation zone 223 as discussed above in relation to FIG. 1 with the exceptions that the apparatus 210 includes a heat exchanger 318, the absorption zone 217 includes two separate chillers 320 and 322, and the stabilizer gas separation zone 223 includes a condenser/chiller 332. As illustrated, the chillers 320 and 322 have corresponding chiller sections 324 and 326.

In particular, the portion 39 of the liquid phase hydrocarbon stream 36 is passed through the heat exchanger 318 for indirect heat exchange with the cooled second intermediate liquid phase hydrocarbon stream 280 to form a partially cooled liquid phase hydrocarbon stream 334 and a partially heated second intermediate liquid phase hydrocarbon stream 336. In an exemplary embodiment, the partially cooled liquid phase hydrocarbon stream 334 has a temperature of from about 15 to about 40° C. and, independently, a pressure of from about 660 to about 2,730 kPa gauge. In an exemplary embodiment, the partially heated second intermediate liquid phase hydrocarbon stream 336 has a temperature of from about 5 to about 65° C. and, independently, a pressure of from about 1,000 to about 1,500 kPa gauge.

The partially heated second intermediate liquid phase hydrocarbon stream 336 is passed along and combined with the intermediate liquid phase hydrocarbon stream 74 to form the combined liquid phase hydrocarbon stream 94. The partially cooled liquid phase hydrocarbon stream 334 is introduced to the chiller 320 and is passed through the chiller section 324 to form the cooled liquid phase hydrocarbon stream 278. The further cooled, further compressed PSA tail gas stream 262 is introduced to the chiller 322 and is passed through the chiller section 326 to form the cooled PSA tail gas stream 277. As discussed above, the cooled PSA tail gas stream 277 and the cooled liquid phase hydrocarbon stream 278 are introduced to the absorber 25 for counter current contact to form the cooled second intermediate liquid phase hydrocarbon stream 280 that is enriched with $C_3/C_4$ hydrocarbons and further comprises $C_5^+$ hydrocarbons and the $H_2$, $C_2^-$ hydrocarbons-containing gas stream 263.

In the stabilizer gas separation zone 223, the stabilizer net gas stream 91 is passed optionally through the dryer 120 to the condenser/chiller 332. The condenser/chiller 332 partially condenses and cools the stabilizer net gas stream 91 to form a partially condensed stabilizer net gas stream 333. In an exemplary embodiment, the partially condensed stabilizer net gas stream 333 has a temperature of from about −28 to about 4° C. and, independently, a pressure of from about 700 to about 1,200 kPa gauge. The partially condensed stabilizer net gas stream 333 is separated in the separator 124 into the light ends gas stream 126 and the $C_3/C_4$ hydrocarbon-rich LPG stream 128 as discussed above.

Figure 3:
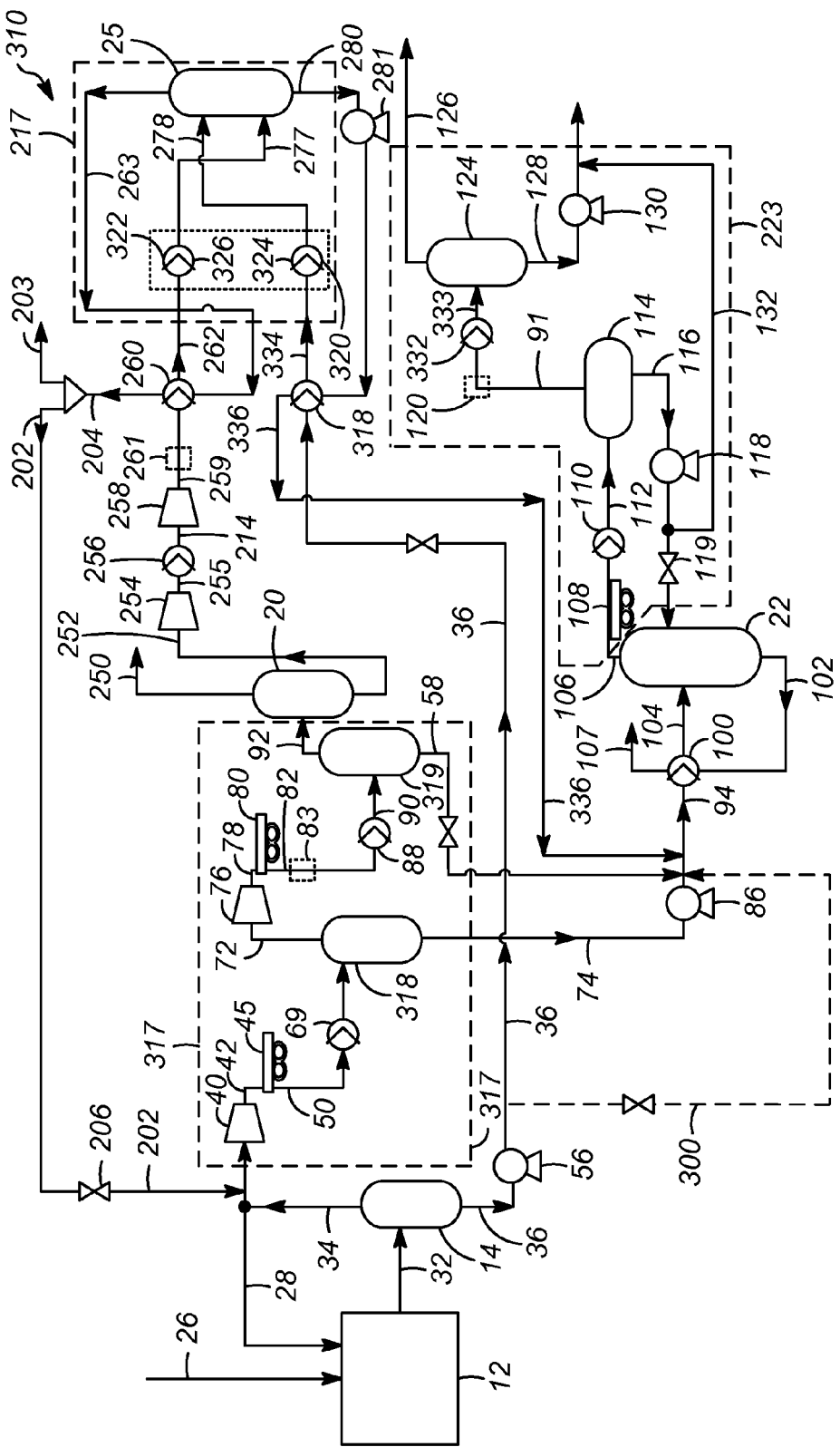
FIG. 3 schematically illustrates an apparatus and a method for reforming of hydrocarbons including recovery of products in accordance with another exemplary embodiment.

Referring to FIG. 3, an apparatus 310 for reforming of hydrocarbons in accordance with another exemplary embodiment is provided. The apparatus 310 is similarly configured to the apparatus 210 including the reforming zone 12, the separation zone 14, the recovery zone 317 including knockout drums 318 and 319, the PSA zone 20, the absorption zone 217 including the absorber 25, the stabilizer 22, and the stabilizer gas separation zone 23 as discussed above in relation to FIG. 2 with the exceptions that the liquid phase hydrocarbon stream 36 is advanced to the absorption zone 217 with zero flow or effectively zero flow to the recovery zone 317 and the intermediate liquid phase hydrocarbon stream 58 is combined with the intermediate liquid phase hydrocarbon stream 74 and the stream 336 to form the combined liquid phase hydrocarbon stream 94. Optionally, the combined liquid phase hydrocarbon stream 94 may also include a portion from the liquid phase hydrocarbon stream 36 via line 300.

With respect to the recovery zone 317, in particular, the partially cooled, compressed net gas phase stream 50 is passed through the cooler 69 to the knockout drum 318 to form intermediate gas phase stream 72 and the intermediate liquid phase hydrocarbon stream 74. Further downstream, the partially cooled, compressed intermediate gas phase stream 82 is passed through the cooler 88 and introduced to the knockout drum 319 to form the $H_2$-rich stream 92 and the intermediate liquid phase hydrocarbon stream 58.

Accordingly, apparatuses and methods for reforming of hydrocarbons with improved recovery of products from a reforming-zone effluent have been described. The exemplary embodiments taught herein separate the reforming-zone effluent in a separation zone to form a net gas phase stream and a liquid phase hydrocarbon stream. The net gas phase stream is separated in a recovery zone for forming an $H_2$-rich stream and a first intermediate liquid phase hydrocarbon stream. The $H_2$-rich stream is contacted with an adsorbent in a pressure swing adsorption (PSA) zone to form an $H_2$-ultra rich stream and a PSA tail gas stream. The PSA tail gas stream and at least a portion of the liquid phase hydrocarbon stream are cooled and contacted in an absorption zone to form a $H_2$, $C_2^-$ hydrocarbons-containing gas stream and a cooled second intermediate liquid phase hydrocarbon stream. The cooled second intermediate liquid phase hydrocarbon stream is further separated to form a $C_5^+$ hydrocarbon-rich reformate stream, a light ends gas stream, and a $C_3/C_4$ hydrocarbon-rich LPG stream.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

What is claimed is:

1. An apparatus for reforming of hydrocarbons including recovery of products, the apparatus comprising:
   a separation zone configured to receive and separate a reforming-zone effluent that comprises $H_2$, $C_4^-$ hydrocarbons, and $C_5^+$ hydrocarbons including aromatics to form a net gas phase stream that comprises $H_2$ and $C_6^-$ hydrocarbons and a liquid phase hydrocarbon stream that comprises $C_5^+$ hydrocarbons including aromatics;
   a recovery zone configured to receive and separate the net gas phase stream for forming an $H_2$-rich stream and a first intermediate liquid phase hydrocarbon stream that is enriched with $C_3/C_4$ hydrocarbons and further comprises $C_5^+$ hydrocarbons;
   a pressure swing adsorption (PSA) zone containing an adsorbent for selectively separating $H_2$ from hydrocarbons, wherein the PSA zone is configured for receiving the $H_2$-rich stream and for contacting the $H_2$-rich stream with the adsorbent to form an $H_2$-ultra rich stream and a PSA tail gas stream that comprises $H_2$, $C_2^-$ hydrocarbons, and some $C_3^+$ hydrocarbons; and
   an absorption zone configured to receive and cool the PSA tail gas stream and at least a portion of the liquid phase hydrocarbon stream to form a cooled PSA tail gas stream and a cooled liquid phase hydrocarbon stream, respectively, wherein the absorption zone comprises an absorber that is configured for contacting the cooled PSA tail gas stream with the cooled liquid phase hydrocarbon stream to extract $C_3/C_4$ hydrocarbons from the cooled PSA tail gas stream to the cooled liquid phase hydrocarbon stream to form a $H_2$, $C_2^-$ hydrocarbons-containing gas stream and a cooled second intermediate liquid phase hydrocarbon stream that is enriched with $C_3/C_4$ hydrocarbons.

2. The apparatus of claim 1, wherein the recovery zone is configured to receive a recycle portion of the $H_2$, $C_2^-$ hydrocarbons-containing gas stream with the net gas phase stream for forming the $H_2$-rich stream and the first intermediate liquid phase hydrocarbon stream.

3. The apparatus of claim 1, wherein the recovery zone is configured to receive and combine the net gas phase stream and a first portion of the liquid phase hydrocarbon stream to extract $C_3/C_4$ hydrocarbons from the net gas phase stream to the first portion of the liquid phase hydrocarbon stream for forming the $H_2$-rich stream and the first intermediate liquid phase hydrocarbon stream, and wherein the absorption zone is configured to receive and cool the PSA tail gas stream and a second portion of the liquid phase hydrocarbon stream to form the cooled PSA tail gas stream and the cooled liquid phase hydrocarbon stream.

4. The apparatus of claim 1, further comprising at least one compressor and at least one cooler, heat exchanger, or combinations thereof cooperatively configured to receive the PSA tail gas stream and to compress and partially cool the PSA tail gas stream to form a further partially cooled, further compressed PSA tail gas stream, and wherein the absorption zone is configured to receive and cool the further partially cooled, further compressed PSA tail gas stream to form the cooled PSA tail gas stream.

5. The apparatus of claim 4, further comprising a dryer that is cooperatively arranged with the at least one compressor and the at least one cooler, heat exchanger, or combinations thereof so as to remove water from the PSA tail gas stream before the further partially cooled, further compressed PSA tail gas stream is introduced to the absorption zone.

6. The apparatus of claim 4, wherein the at least one compressor and the at least one cooler, heat exchanger, or combinations thereof are cooperatively configured to receive the PSA tail gas stream and to compress and partially cool the PSA tail gas stream to form a partially cooled, further compressed PSA tail gas stream, and wherein the at least one cooler, heat exchanger, or combinations thereof comprises a PSA tail gas heat exchanger that is configured for indirect heat exchange between the partially cooled, further compressed PSA tail gas stream and the $H_2$, $C_2^-$ hydrocarbons-containing gas stream to form the further partially cooled, further compressed PSA tail gas stream and a partially heated $H_2$, $C_2^-$ hydrocarbons-containing gas stream.

7. The apparatus of claim 4, wherein the absorption zone comprises:
at least one heat exchanger, first chiller section, or combination thereof configured to receive and cool the further partially cooled, further compressed PSA tail gas stream to form the cooled PSA tail gas stream; and
at least one heat exchanger, second chiller section, or combinations thereof configured to receive and cool the at least the portion of the liquid phase hydrocarbon stream to form the cooled liquid phase hydrocarbon stream.

8. The apparatus of claim 7, wherein the at least one heat exchanger, second chiller section, or combination thereof comprises:
a heat exchanger configured for indirect heat exchange between the at least the portion of the liquid phase hydrocarbon stream and the cooled second intermediate liquid phase hydrocarbon stream to form a partially cooled liquid phase hydrocarbon stream and a partially heated second intermediate liquid phase hydrocarbon stream; and
a second chiller section configured to receive and cool the partially cooled liquid phase hydrocarbon stream to form the cooled liquid phase hydrocarbon stream.

9. The apparatus of claim 1, further comprising:
at least one heater, heat exchanger, or combinations thereof configured to receive and heat the cooled second intermediate liquid phase hydrocarbon stream to form a heated second intermediate liquid phase hydrocarbon stream;
a stabilizer configured to receive and separate the heated second intermediate liquid phase hydrocarbon stream to form a $C_5^+$ hydrocarbon-rich reformate stream that comprises primarily $C_5^+$ hydrocarbons and a stabilizer gas stream that comprises $H_2$ and $C_4^-$ hydrocarbons; and
a stabilizer gas separation zone configured to receive and partially condense and cool at least a portion of the stabilizer gas stream to form a partially condensed stabilizer net gas stream, wherein the stabilizer gas separation zone comprises:
a separator configured to receive and separate the partially condensed stabilizer net gas stream to form a $C_3/C_4$ hydrocarbon-rich LPG stream that comprises primarily $C_3/C_4$ hydrocarbons and a light ends gas stream that comprises $H_2$ and $C_2^-$ hydrocarbons.

10. The apparatus of claim 9, wherein the stabilizer gas separation zone comprises at least one heat exchanger, chiller, cooler, or combination thereof configured to receive and partially condense and cool the at least the portion of the stabilizer gas stream to form the partially condensed stabilizer net gas stream.

11. The apparatus of claim 10, wherein the at least one heat exchanger, chiller, cooler, or combination thereof is a stabilizer gas separation zone heat exchanger configured for indirect heat exchange between the cooled second intermediate liquid phase hydrocarbon stream and the at least the portion of the stabilizer gas stream to form a first partially heated, second intermediate liquid phase hydrocarbon stream and the partially condensed stabilizer net gas stream, and wherein the at least one heater, heat exchanger, or combinations thereof comprises the stabilizer gas separation zone heat exchanger.

12. The apparatus of claim 11, wherein the absorption zone comprises:
an absorption zone heat exchanger configured for indirect heat exchange between the PSA tail gas stream and the first partially heated, second intermediate liquid phase hydrocarbon stream to form a partially cooled PSA tail gas stream and a second partially heated, second intermediate liquid phase hydrocarbon stream, and wherein the at least one heater, heat exchanger, or combinations thereof further comprises the absorption zone heat exchanger; and
a chiller section configured to receive and cool the partially cooled PSA tail gas stream to form the cooled PSA tail gas stream.

13. The apparatus of claim 12, further comprising a stabilizer heat exchanger that is configured for indirect heat exchange between the second partially heated, second intermediate liquid phase hydrocarbon stream and the $C_5^+$ hydrocarbon-rich reformate stream to form the heated second intermediate liquid phase hydrocarbon stream, wherein the at least one heater, heat exchanger, or combinations thereof further comprises the stabilizer heat exchanger.

14. A method for reforming of hydrocarbons including recovery of products, the method comprising the steps of:

separating a reforming-zone effluent that comprises $H_2$, $C_4^-$ hydrocarbons, and $C_5^+$ hydrocarbons including aromatics to form a net gas phase stream that comprises $H_2$ and $C_6^-$ hydrocarbons and a liquid phase hydrocarbon stream that comprises $C_5^+$ hydrocarbons including aromatics;

separating the net gas phase stream for forming an $H_2$-rich stream and a first intermediate liquid phase hydrocarbon stream that is enriched with $C_3/C_4$ hydrocarbons and further comprises $C_5^+$ hydrocarbons;

contacting the $H_2$-rich stream with an adsorbent that selectively separates $H_2$ from hydrocarbons to form an $H_2$-ultra rich stream and a pressure swing adsorption (PSA) tail gas stream that comprises $H_2$, $C_2^-$ hydrocarbons, and some $C_3^+$ hydrocarbons;

cooling the PSA tail gas stream to form a cooled PSA tail gas stream;

cooling at least a portion of the liquid phase hydrocarbon stream to form a cooled liquid phase hydrocarbon stream; and contacting the cooled PSA tail gas stream with the cooled liquid phase hydrocarbon stream to extract $C_3/C_4$ hydrocarbons from the cooled PSA tail gas stream to the cooled liquid phase hydrocarbon stream and to form a $H_2$, $C_2^-$ hydrocarbons-containing gas stream and a cooled second intermediate liquid phase hydrocarbon stream that is enriched with $C_3/C_4$ hydrocarbons.

15. The method of claim 14, further comprising the step of:
compressing the PSA tail gas stream to form a compressed PSA tail gas stream, and wherein the steps of compressing and cooling the PSA tail gas stream cooperatively comprise:
forming a further partially cooled, further compressed PSA tail gas stream; and
cooling the further partially cooled, further compressed PSA tail gas stream to form the cooled PSA tail gas stream.

16. The method of claim 15, wherein the steps of compressing and cooling the PSA tail gas stream comprise forming the further partially cooled, further compressed PSA tail gas stream having a temperature of from about 30 to about 150° C.

17. The method of claim 15, wherein the steps of compressing and cooling the PSA tail gas stream comprise forming the further partially cooled, further compressed PSA tail gas stream having a pressure of from about 690 to about 2,760 kPa gauge.

18. The method of claim 15, wherein the step of cooling the further partially cooled, further compressed PSA tail gas stream comprises forming the cooled PSA tail gas stream having a temperature of from about −28 to about 4° C.

19. The method of claim 15, wherein the step of cooling the further partially cooled, further compressed PSA tail gas stream comprises forming the cooled PSA tail gas stream having a pressure of from about 630 to about 2,700 kPa gauge.

20. A method for reforming of hydrocarbons including recovery of products, the method comprising the steps of:
combining a gas phase stream that comprises $H_2$ and $C_6^-$ hydrocarbons with a first portion of a liquid phase hydrocarbon stream that comprises $C_5^+$ hydrocarbons including aromatics to extract $C_3/C_4$ hydrocarbons from the gas phase stream to the first portion of the liquid phase hydrocarbon stream for forming an $H_2$-rich stream that comprises primarily $H_2$ and an intermediate liquid phase hydrocarbon stream that is enriched with $C_3/C_4$ hydrocarbons and further comprises $C_5^+$ hydrocarbons;

contacting the $H_2$-rich stream with an adsorbent that selectively separates $H_2$ from hydrocarbons and that is contained in a pressure swing adsorption (PSA) zone to form an $H_2$-ultra rich stream and a PSA tail gas stream that comprises $H_2$, $C_2^-$ hydrocarbons, and some $C_3^+$ hydrocarbons;

cooling the PSA tail gas stream to form a cooled PSA tail gas stream;

cooling a second portion of the liquid phase hydrocarbon stream to form a cooled liquid phase hydrocarbon stream; and contacting the cooled PSA tail gas stream with the cooled liquid phase hydrocarbon stream in an absorber to extract $C_3/C_4$ hydrocarbons from the cooled PSA tail gas stream to the cooled liquid phase hydrocarbon stream and to form a $H_2$, $C_2^-$ hydrocarbons-containing gas stream and a cooled second intermediate liquid phase hydrocarbon stream that is enriched with $C_3/C_4$ hydrocarbons.

* * * * *